United States Patent [19]

Zimmer et al.

[11] Patent Number: 5,254,731
[45] Date of Patent: Oct. 19, 1993

[54] SUBSTITUTED 3,4-DIHYDRONAPHTHALENES, PHARMACEUTICAL COMPOSITIONS CONTAINING THEM, AND PREPARATION PROCESSES

[75] Inventors: Oswald Zimmer, Dueren; Werner Vollenberg; Johannes Schneider, both of Stolberg, all of Fed. Rep. of Germany

[73] Assignee: Gruenenthal GmbH, Aachen, Fed. Rep. of Germany

[21] Appl. No.: 911,625

[22] Filed: Jul. 10, 1992

[30] Foreign Application Priority Data

Jul. 23, 1991 [DE] Fed. Rep. of Germany ....... 4124345

[51] Int. Cl.⁵ .............................................. C07C 53/06
[52] U.S. Cl. .................................. 562/621; 562/623; 514/507
[58] Field of Search ................. 562/621, 623; 514/507

[56] References Cited

FOREIGN PATENT DOCUMENTS

| | | |
|---|---|---|
| 0279263 | 8/1988 | European Pat. Off. . |
| 0292699 | 11/1988 | European Pat. Off. ............. 562/623 |
| 0408760 | 1/1991 | European Pat. Off. . |
| 0452908 | 10/1991 | European Pat. Off. . |
| 2-07494 | 1/1990 | Japan .................................. 562/621 |

OTHER PUBLICATIONS

Jakschik et al., Biochem. Biophys. Res. Commun., 102, 624 (1981).
Tateson et al., in Brit. J. Pharmacol., 94, 528 (1988).
J. B. Summers et al., J. Med. Chem., 31, 1960 (1988).

*Primary Examiner*—José G. Dees
*Assistant Examiner*—Keith MacMillan

*Attorney, Agent, or Firm*—Evenson, McKeown, Edwards & Lenahan

[57] ABSTRACT

Substituted 3,4-dihydronaphthalenes of the formula I

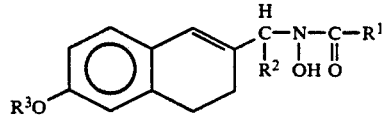

wherein $R^1$ is a methyl or an amino group, $R^2$ represents a hydrogen atom or a methyl group, and $R^3$ is a linear or branched chain alkyl residue having 1 to 4 carbon atoms, an allyl or a crotyl group or a cyclopentyl group are disclosed which specifically inhibit 5-lipoxygenase and are useful in pharmaceutical compositions for prophylaxis and treatment of disorders attributable to the action of leucotrienes. The dihydronaphthalenes may be prepared by reacting a compound of formula II

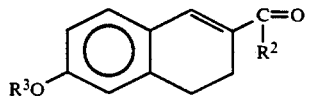

with hydroxylamine or a salt thereof to form the corresponding oxime, reducing the oxime to a hydroxylamine of formula III

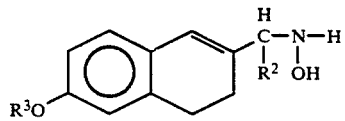

and introducing a —CO—$R^1$ group.

14 Claims, No Drawings

SUBSTITUTED 3,4-DIHYDRONAPHTHALENES, PHARMACEUTICAL COMPOSITIONS CONTAINING THEM, AND PREPARATION PROCESSES

BACKGROUND OF THE INVENTION

Polyunsaturated higher fatty acids such as arachidonic acid serve in the metabolism of mammals, including man, as substrates for the formation of physiologically important eicosanoids such as prostaglandins and leucotrienes (a group of compounds also known as "Slow Reacting Substance of Anaphylaxis" or "SRS-A"). The pathway to prostaglandins is catalyzed by cyclooxygenase (also named "prostaglandin synthetase") whereas the pathway to leucotrienes is catalyzed by 5-lipoxygenase.

The prostaglandins are products having known beneficial functions in mammals. On the other hand, the leucotrienes or SRS-A, respectively, are known to cause allergic reactions, bronchoconstrictions, inflammations, asthma and numerous other harmful effects. Accordingly, there is a need for chemically and metabolically stable agents which in the living organism have no effect on the biosynthesis of prostaglandins but which selectively or specifically inhibit the activity of 5-lipoxygenase and thus prevent the formation of the undesired leucotrienes. However, up to now this problem has not yet been solved in an adequate manner.

SUMMARY OF THE INVENTION

It is therefore the object of the present invention to provide new, pharmacologically active substances which act to selectively or specifically inhibit the action of leucotrienes.

It is also an object of the invention to provide active substances and pharmaceutical compositions for treating allergic reactions, bronchoconstrictions, inflammations, asthma, or the like.

Another object of the invention is to provide pharmacologically active agents which exhibit a shock inhibiting effect.

A further object of the invention is to provide methods of treating disorders in mammals attributable to the action of leucotrienes.

These and other objects of the invention are achieved by providing substituted 3,4-dihydronaphthalenes corresponding to the formula I

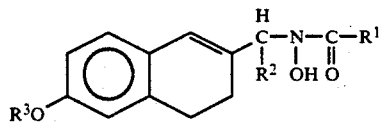

wherein $R^1$ is a methyl group or an amino group;

$R^2$ represents a hydrogen atom or a methyl group, and $R^3$ is a linear or branched chain alkyl group having 1 to 4 carbon atoms, an allyl or crotyl group, or a cyclopentyl group.

According to a further aspect of the invention, the objects are achieved by providing a pharmaceutical composition for parenteral, oral, rectal, topical or intranasal administration comprising an effective 5-lipoxygenase inhibiting amount of at least one substituted 3,4-dihydronaphthalene corresponding to the formula I

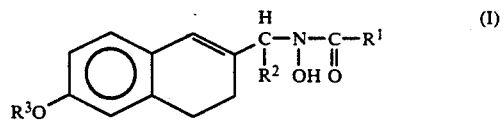

wherein $R^1$ is a methyl group or an amino group;

$R^2$ represents a hydrogen atom or a methyl group, and $R^3$ is a linear or branched chain alkyl group having 1 to 4 carbon atoms, an allyl or crotyl group, or a cyclopentyl group, and at least one pharmaceutical carrier or excipient.

In accordance with yet another aspect of the invention, the objects are achieved by providing a process for preparing a substituted 3,4-dihydronaphthalene corresponding to the formula I

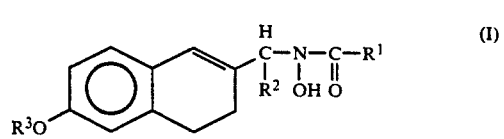

wherein $R^1$ is a methyl group or an amino group;

$R^2$ represents a hydrogen atom or a methyl group, and $R^3$ is a linear or branched chain alkyl group having 1 to 4 carbon atoms, an allyl or crotyl group, or a cyclopentyl group, said process comprising reacting a compound of formula II

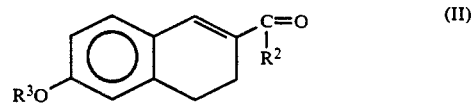

with hydroxylamine or a salt thereof in the presence of a base to form the corresponding oxime, reducing the resulting oxime with a boron-containing reducing agent in the presence of an acid to a hydroxylamine of formula III

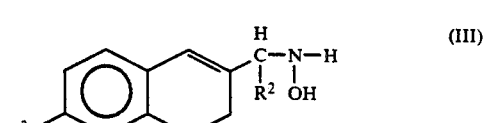

and introducing a —CO—$R^1$ group.

The invention also includes methods for treating patients suffering from disorders attributable to the action of leucotrienes comprising administering to said patients an effective 5-lipoxygenase inhibiting amount of at least one substituted 3,4-dihydronaphthalene corresponding to the formula I

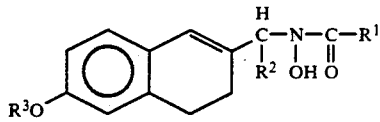

wherein

R¹ is a methyl group or an amino group;

R² represents a hydrogen atom or a methyl group, and

R³ is a linear or branched chain alkyl group having 1 to 4 carbon atoms, an allyl or crotyl group, or a cyclopentyl group.

DETAILED DESCRIPTION OF PREFERRED EMBODIMENTS

The present invention relates to certain substituted 3,4-dihydronaphthalenes which are chemically, and when used as therapeutics metabolically, stable compounds and which also exhibit further biologically and pharmaceutically valuable properties, a specific inhibiting effect on 5-lipoxygenase and surprisingly a shock inhibiting effect as well as a distinct the rate of shock mortality decreasing effect. The compounds according to the invention correspond to the general formula I

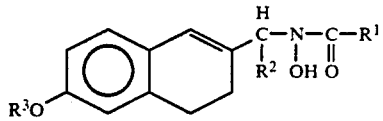

wherein R¹ is the methyl or the amino group, R² represents a hydrogen atom or the methyl group, and R³ is a linear or branched chain alkyl group having 1 to 4 carbon atoms, an allyl or crotyl group or a cyclopentyl group. Compounds in which R³ represents a methyl group are preferred, and compounds in which R¹ is an amino group are particularly preferred. N-hydroxy-N-[(6-methoxy-3,4-dihydronaphth-2-yl)methyl]urea is an especially preferred compound which is especially suitable for treating patients suffering from asthma.

Substituted 3,4-dihydronaphthalenes of formula I show a specific inhibiting effect on 5-lipoxygenase which was determined e.g. by in vitro experiments.

To determine the inhibition of 5-lipoxygenase rat basophilic leukemia cells were cultured in vitro, harvested by centrifugation, washed with 50 mM potassium phosphate buffer of pH 7.4, and then suspended in this buffer at $1 \times 10^7$ cells/ml. To 1 ml aliquots of this suspension there was added indomethacin (10 µM) and calcium chloride (2 mM), and then the mixture was incubated for 3 minutes in the absence or presence of a compound according to the invention in a concentration range of from 0,1 µM to 100 µM and thereafter for 10 minutes with 20 µM of [$^{14}$C]-arachidonic acid and 20 µM of the calcium ionophore A23187. The reaction was stopped by adding 20 µl of glacial acetic acid, and then the mixture was extracted with ethyl acetate to isolate the metabolites of arachidonic acid formed by the enzymatic action of 5-lipoxygenase. These were separated by thin layer chromatography using a solvent mixture known to be suitable for leucotriene analysis [c.f. Jakschik et al., *Biochem. Biophys. Res. Commun.*, Vol. 102, p. 624 (1981)].

The distribution of the radioactivity to the different metabolites was measured using a TLC Linear Analyzer. By relating the percentages of the amount of the products formed under the action of 5-lipoxygenase (5-HETE, isomers of LTB₄) in the absence as well as in the presence of a compound according to the invention in different concentrations, the IC₅₀-values, i.e. the concentrations causing an inhibition of 50% of 5-lipoxygenase were determined. For standardization these values were correlated with the IC₅₀-values determined in the same manner for the standard compound nordihydroguaiaretic acid. Most of the substituted 3,4-dihydronaphthalenes of formula I have IC₅₀-values of 1 µmolar or less.

The effect of the compounds according to the invention on the activity of cyclooxygenase was tested using a suspension of sheep seminal vesicle microsomes in 50 µM potassium phosphate buffer of pH 7.0 which was incubated either with a compound according to the invention or with a solvent only and [$^{14}$C]-arachidonic acid. It has been found that none of the substituted 3,4-dihydronaphthalenes of formula I in concentrations up to 500 µmolar had an inhibiting effect on cyclooxygenase.

The results of the aforementioned experiments show that the IC₅₀-values for the inhibition of cyclooxygenase are significantly higher than the IC₅₀-values for inhibiting 5-lipoxygenase, i.e. the substituted 3,4-dihydronaphthalenes of formula I are very specific in their inhibition of activity of 5-lipoxygenase.

The bioavailability of the compounds of formula I after oral administration was characterized by means of the following ex vivo biochemical assessment method described by Tateson et al. in *Brit. J. Pharmacol.*, Vol. 94, p. 528 (1988):

Compounds of formula I were orally administered to male rats (Wistar strain). One hour later the rats were bled by heart puncture in lethal CO₂-narcosis. The 5-lipoxygenase reaction was triggered by adding the calcium-ionophore A23187 to an end concentration of 15 µg/ml to aliquots of rat whole blood and subsequently incubating for 30 minutes at 37° C. in a water bath. At the end of the incubation the samples were centrifuged to collect the cell free plasma. The concentration of the immunoreactive LTB₄ (iLTB₄ ng/ml) in each plasma sample was determined by radioimmunoassay ($^3$H-LTB₄-RIA, Amersham) by means of a LTB₄-standard curve in diluted rat plasma. In order to determine the percent inhibition of ex vivo iLTB₄-formation in whole blood of rats treated with a compound of formula I, rats orally treated with an appropriate vehicle solution were included in all experiments, aliquots of their blood were run in parallel and were processed in the same way as described. The mean iLTB₄-formation per ml plasma of these vehicle treated rats was taken as the 100 percent value of normal 5-lipoxygenase activity. The percent inhibition of the ex vivo iLTB₄-formation after oral administration of a compound of formula I was calculated according to the following formula:

$$\% \text{ inhib} = 100 - [100 \times (Q \div C)]$$

where Q represents the mean iLTB₄ contents in ng iLTB₄ per ml plasma of the test rats treated with a compound of formula I, and C represents the mean iLTB₄ contents in ng iLTB₄ per ml plasma of the control rats treated only with the vehicle. ED₅₀-values (i.e. the concentrations after oral administration which cause a 50% inhibition of the ex vivo iLTB₄-formation) of 13.0 mg/kg, 20.0 mg/kg and 14.7 mg/kg were determined for the substituted 3,4-dihydronaphthalenes prepared according to preparative Examples 2 and 3, respectively.

The anti-asthmatic effect of compounds according to the invention was tested in anesthetized and ventilated guinea pigs. To induce an asthmatic reaction, the animals were passively sensitized by a single intraperitoneal injection of anti-ovalbumin serum. After 48 hours the asthmatic reaction was elicited by intravenous challenge with 0.2 mg/kg of ovalbumin. The immediately resulting bronchoconstriction was measured as an increase in intratracheal pressure. Effects caused by histamine, serotonin and sympathic counterreaction were eliminated by intravenous pretreatment with 2.15 mg/kg of mepyramine, 46.4 mg/kg of propranolol, 4.64 mg/kg of atropine and 1 mg/kg of methysergide, all administered 5 minutes before challenge. Substituted 3,4-dihydronaphthalenes were orally administered 60 minutes before the administration of ovalbumin. For the inhibition of the bronchoconstriction elicited by ovalbumin $ED_{40}$-values (i.e. effective doses causing a 40% average inhibition of the bronchoconstriction) of 33,5 mg/kg, 275 mg/kg and 368 mg/kg were determined for the substituted 3,4-dihydronaphthalenes prepared according to Examples 3, 6a and 6e, respectively.

To evaluate the effects of compounds according to the invention on septic shock, endotoxin/galactosamine-induced hepatitis in mice was used as test model. In this model, intravenous injection of 300 μg/kg of endotoxin (lipopolysaccharide from *S. abortus equi*) in combination with 700 mg/kg of galactosamine induces a hepatitis in conscious mice, which is demonstrated 8 hours after the administration of endotoxin by increased activities of liver specific enzymes (glutamate-pyruvate-transaminase, GPT; and sorbitol-dehydrogenase, SDH) in the serum. Intraperitoneal administration of compounds of formula I 30 minutes before, simultaneously with, and 2, 4 and 6 hours after administration of the endotoxin inhibits the hepatitis-induced increase of the activities of these enzymes in the serum. On administration of compounds of formula I in doses of 10 mg/kg for each of the five administrations, the following percentage inhibitions of the increase of the enzymatic activities of GPT and SDH were achieved (the increase of enzymatic activities in control animals who had been treated five times with a solution containing 1% by weight of sodium carboxymethylcellulose was set at 100%):

| Example | Inhibition of increase of the enzymatic activity of | |
|---|---|---|
| | GPT | SDH |
| 1 | 54% | 41% |
| 2 | 56% | 69% |
| 3 | 78% | 57% |

Administration of substituted 3,4-dihydronaphthalenes of formula I also caused a reduced shock mortality.

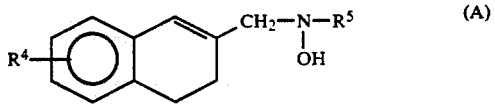

(A)

in which $R^4$ may represent an aryloxy or an aryl(lower)alkoxy group and $R^5$ may represent a carbamoyl or an acetyl group are described in European patent application No. EP 408,760. The compounds of formula A in which $R^4$ represents a benzyloxy group in the 6 position of the 3,4-dihydronaphthalene moiety and $R^5$ is either a carbamoyl (A1) or an acetyl (A2) group have been used in the aforementioned test model involving endotoxin/galactosamine-induced hepatitis. The urea compound A1 did not cause either an inhibition of GPT and SDH or a decrease in the shock mortality, and the acetyl compound A2 caused only a low inhibition of GPT (16%) and SDH (32%) and showed no detectable influence on shock mortality.

The results of these comparative experiments surprisingly show that in comparison to the known compounds of formula A with a similar structure, substituted 3,4-dihydronaphthalenes according to the invention exhibit a marked effect on septic and anaphylactic shock.

The compounds according to the invention exhibit various physiologically valuable properties such as anti-anaphylactic and anti-asthmatic effects.

Due to their chemical, and when used as therapeutics metabolic, stability substituted 3,4-dihydronaphthalenes of formula I are storable and suitable for use as medicaments such as anti-anaphylactics, anti-asthmatics and agents for use in prophylaxis and treatment of shock.

The compounds of formula I have a low degree of toxicity which is observed only at far higher doses than those to be administered for therapeutic or prophylactic purposes. Accordingly these compounds can be administered to humans and animals.

The invention also relates to pharmaceutical compositions or medicaments containing one or more of the substituted 3,4-dihydronaphthalenes of formula I. The dosage of this active ingredient to be administered to a patient depends, for instance, on the body weight, on the route and form of administration, on the indication, and on the state of disease in the individual to be treated. Taking these factors into consideration, the typical unit dosage form of a pharmaceutical composition according to the present invention will contains an amount in the range from about 0.01 to 1000 mg of the active ingredient. Compositions for parenteral, oral or rectal administration typically contain an amount in the range from about 0.1 to 1000 mg, and those for topical or inhalative administration typically contain about 0.01 to 100 mg per unit dose.

Pharmaceutical compositions for parenteral administration may be solutions or suspensions, but may also be dry formulations suitable for easy reconstitution.

Spray forms are very useful application forms for intranasal or oral administration of the compounds of formula I or for administering these substances to the bronchia.

Compositions for oral administration such as tablets, dragees, capsules, granules, drops and syrups are very suitable for prophylactic or therapeutic administration of the compounds of formula I in several situations. Other compositions such as suppositories or compositions for percutaneous administration of the compounds of formula I, such as plasters or the like containing a solution of the active ingredient and optionally a known membrane penetration enhancer (such as an N-alkyl lactam) are also very useful in many cases. The pharmaceutical compositions described above for oral, rectal, or percutaneous administration of the compounds of formula I preferably may be formulated in such a way that at least a portion of the active ingredient has a delayed release. Thus, a steady supply of the active ingredient to the patient for a longer period of time, for instance 24 hours, can be achieved.

All of the general types of pharmaceutical compositions to which the invention is applicable as well as the preparation of these compositions are known per se. Since the compounds of formula I are chemically stable, their incorporation into such pharmaceutical compositions in the form and dosage desired poses no problems for an ordinarily skilled pharmacist. In the production of pharmaceutical compositions according to the invention conventionally used inorganic or organic adjuvants such as carriers, diluents, solvents, binders, lubricants, tablet disintegrating agents, colors, and/or flavorings are formulated together with the active ingredient of formula I in accordance with accepted standards in a known manner. Compositions for parenteral use must be sterile and, if prepared in liquid form, isotonic.

In the process of preparing compounds of formula I according to the invention, a compound of formula II

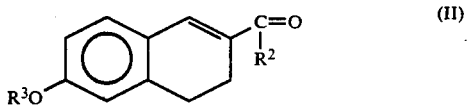

in which $R^2$ and $R^3$ have the meanings given above is reacted with hydroxylamine or a salt thereof in the presence of a base to form the corresponding oxime which is reduced with a boron-containing reducing agent in the presence of an acid to a hydroxylamine of formula III

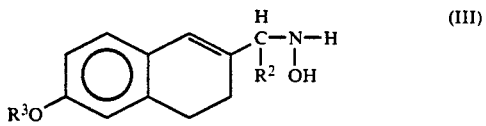

in which the residue $-CO-R^1$ is introduced.

The conversion of a compound of formula II to the corresponding oxime is carried out in a known manner, for instance in an alcoholic or an aqueous-alcoholic solution in the presence of a base, e.g. pyridine, potassium carbonate or sodium acetate, at temperatures of from 20° to 60° C.

The reduction is preferably performed by means of boron hydrides, particularly sodium cyanoborohydride, in the presence of acetic acid or ethanolic hydrochloric acid at temperatures of from 20° to 60° C., or in an alcoholic solution with a borane-amine complex, e.g. borane-trimethylamine complex or borane-pyridine complex, or with borane-tetrahydrofuran complex in the presence of an acid, e.g. 6M hydrochloric acid at temperatures of from 0° to 50° C. (J. B. Summers et al., *J. Med. Chem.*, Vol. 31, p. 1960 (1988)).

The hydroxylamine of formula III is transformed into the corresponding substituted 3,4-dihydronaphthalene of formula I by introducing the residue $-CO-R^1$, i.e. by attaching a $-CO-R^1$ group to the amino nitrogen atom of the compound of formula III.

To prepare compounds of formula I in which $R^1$ represents an amino group (N-hydroxy ureas) a hydroxylamine of formula III is reacted with trimethylsilyl isocyanate in the presence of an inert solvent, preferably a cyclic ether such as tetrahydrofuran or 1,4-dioxane, while heating to temperatures between 20° C. and the boiling temperature of the solvent. The resulting intermediate then is hydrolyzed, e.g. by treatment with a saturated aqueous solution of ammonium or sodium chloride, to obtain the desired compound of formula I in which $-R^1$ is $-NH_2$.

Alternatively N-hydroxy ureas may be obtained in a known manner by reacting a hydroxylamine of formula III either with potassium or sodium cyanate in an acidic solution or with phosgene or a lower alkyl or benzyl chloroformate in the presence of an agent capable of binding acids, e.g. sodium or potassium carbonate, followed by treatment with ammonia or an ammonia releasing compound, e.g. ammonium carbonate.

To prepare compounds of formula I in which $R^1$ represents a methyl group (acetohydroxamic acids) a hydroxylamine of formula III, optionally without isolation from the reaction mixture in which it was prepared, is reacted with an acetylating agent, preferably acetic anhydride or acetyl chloride, in the presence of an agent capable of binding acids, e.g. pyridine or quinoline, whereby a compound of formula IV

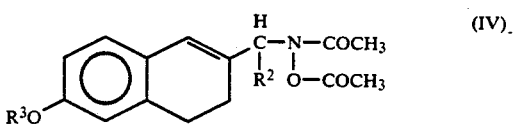

is formed. On treatment with a base in the presence of an alcoholic solvent, e.g. methanol or ethanol, at temperatures of about 20° to 60° C., the 0 acetyl group is split off, and the desired compound of formula I in which $R^1$ is methyl is obtained. Suitable bases include, for example, potassium, sodium or lithium hydroxide, sodium or potassium carbonate, which optionally may be added in the form of an aqueous 0.1 to 1 M solution or an alcoholic solution, to a compound of formula IV.

The starting compounds of formula II may be prepared in a known manner by reducing a 1-tetralone derivative of formula V

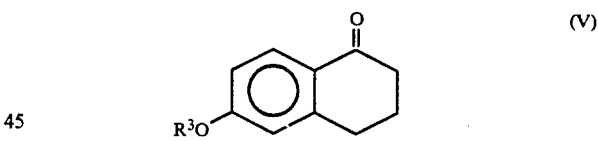

with a complex metal hydride, e.g. sodium borohydride in methanol or ethanol or lithium aluminium hydride in diethyl ether, tetrahydrofuran or any other suitable ether, to a 1,2,3,4-tetrahydro-1-naphthol derivative of formula VI

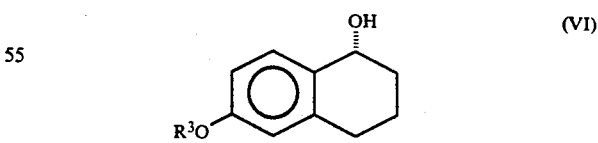

A compound of formula II in which $R^2$ represents a hydrogen atom is obtained in a high yield from a compound of formula VI by Vilsmeyer formylation with e.g. phosphorus oxychloride/dimethylformamide or N-methylformanilide at temperatures between 0° and 70° C.

A compound of formula II in which $R^2$ represents the methyl group may be obtained by reacting a compound of formula II in which $R^2$ is a hydrogen atom with methyl magnesium iodide or methyl magnesium bromide in diethyl ether and oxidizing the resulting secondary alcohol with e.g. 2,3-dichloro-5,6-dicyano-p-benzoquinone in benzene or toluene at 20° C.

EXAMPLES

All temperature references are uncorrected. The $^1$H-nuclear magnetic spectra ($^1$H-NMR) were measured at 300 MHz. The chemical shifts are given in ppm.

Petroleum ether having a boiling range of from 50° C. to 70° C. was used. In column chromatography, silica gel ("Kieselgel 60", 0.040 to 0.063 mm from E. Merck, of Darmstadt, Germany) was used as the stationary phase. In most instances the reactions were monitored by thin layer chromatography on plates precoated with silica gel ("HPTLC Fertigplatten, Kieselgel 60 F 254" from E. Merck, of Darmstadt, Germany). The solvents used in these cases are indicated in the examples by "(TLC: ... )". The ratio of the components of the solvent mixtures used in all of the chromatographic procedures is given in volume/volume.

EXAMPLE 1

N-[(6-methoxy-3,4-dihydronaphth-2-yl)methyl]acetohydroxamic acid a) 1-hydroxy-6-methoxy-1,2,3,4-tetrahydronaphthalene To a solution of 10.68 g of 6-methoxy-1-tetralone in 180 ml of methanol were added while stirring in small portions 4.56 g of sodium borohydride in such a manner that the temperature did not exceed 30° C. After stirring for an additional hour at 20° C. the volume was reduced to 30 ml by evaporation, diluted with 200 ml of water and extracted four times with 50 ml portions of ethyl acetate. The extracts were washed with an aqueous saturated solution of sodium chloride and dried over sodium sulfate. After evaporating under vacuum 10.34 g (96.2% of the theoretical yield) of 1-hydroxy-6-methoxy-1,3,3,4-tetrahydronaphthalene were obtained in the form of an oil.

$^1$H-NMR (CDCl$_3$):
1.68-2.03 (m, 4H) CH$_2$);
2.63-2.87 (m, 2H, CH$_2$-aromat);
3.78 (s, 3H, OCH$_3$);
4.70-4.78 (m, 1H, OCH);
6.61-6.62 (d, 1H, aromat.);
6.74-6.78 (d,d, 1H, aromat.);
7.31-7.34 (d, 1H, aromat.)

b) 6-methoxy-3,4-dihydronaphth-2-aldehyde

To a solution of 10.0 g of the compound prepared according to Example 1a in 35 ml of dimethylformamide were added dropwise while stirring at a temperature between 0° and 5° C. under an atmosphere of dry nitrogen a freshly prepared mixture of 5.3 ml of phosphorous oxychloride and 11.6 ml of dimethylformamide. Over the course of 1 hour the mixture was heated to 75° to 80° C. and stirred at this temperature until the reaction was completed (TLC: petroleum ether/diethyl ether—1:1). Then the mixture was allowed to cool, and after adding a solution of 36.6 g of sodium acetate in 85 ml of water, the mixture was extracted with ethyl acetate. The extracts were washed with an aqueous saturated solution of sodium chloride and dried over sodium sulfate. After chromatography with petroleum ether/diethyl ether (1:1), 9.92 g (94.5% of the theoretical yield) of the aldehyde were obtained in the form of yellow crystals melting at 48°-49° C.

$^1$H-NMR (CDCl$_3$):
2.51-2.57 (m, 2H, CH$_2$);
2.82-2.87 (t, 2H, CH$_2$);
3.83 (s, 3H, OCH$_3$);
6.75-6.79 (m, 2H, aromat.);
7.21-7.23 (m, 1H, aromat.);
7.24 (s, 1H, olefin.);
9.60 (s, 1H, CHO)

c) 6-methoxy-3,4-dihydronaphth-2-aldehyde-oxime

A solution of 9.88 g of the aldehyde prepared according to Example 1b, 8.61 g of sodium acetate and 9.18 g of hydroxylamine hydrochloride in a mixture of 75 ml of methanol, 75 ml of tetrahydrofuran and 90 ml of water was stirred at a bath temperature of 60° C. for 8 hours. After evaporation of the solvent, the resulting residue was dissolved in 200 ml of ethyl acetate and washed with water and an aqueous saturated solution of sodium chloride. After drying over sodium sulfate, evaporating under vacuum and recrystallizing from diethyl ether/n hexane, 9.45 g (88.6% of the theoretical yield) of the oxime were obtained in the form of yellow crystals melting at 169°-172° C.

$^1$H-NMR (CDCl$_3$):
2.56-2.61 (t, 2H, CH$_2$);
2.82-2.88 (t, 2H, CH$_2$);
3.82 (s, 3H, OCH$_3$);
6.61 (s, 1H, olefin.);
6.70-6.73 (m, 2H, aromat.);
7.04-7.07 (m, 1H, aromat.);
7.89 (s, 1H, N=CH)

d) N-[(6-methoxy-3,4-dihydronaphth-2-yl)methyl]acetohydroxamic acid

To a solution of 9.35 g of the oxime prepared according to Example 1c in 100 ml of acetic acid were added at a bath temperature of 50°-55° C. while stirring under an atmosphere of dry nitrogen in small portions 4.35 g of sodium cyanoborohydride. After stirring for an additional hour, the mixture was allowed to cool, and after adding 8.75 ml of acetic anhydride the mixture was stirred for a further 12 hours. Then the mixture was evaporated under vacuum, the residue diluted with 150 ml of water and extracted three times with 50 ml portions of ethyl acetate. The extracts were washed with aqueous saturated solutions of sodium hydrogen carbonate and of sodium chloride, and then dried over sodium sulfate. The compound of formula IV was isolated from the residue obtained after evaporation of the solvent by chromatography with ethyl acetate/petroleum ether (2:1) and then dissolved in 100 ml of methanol. After adding 100 ml of an aqueous solution containing 10% by weight of sodium carbonate, the mixture was heated, while stirring, for 2 hours at 60° C. The resulting residue obtained upon evaporation under a vacuum was recrystallized from diethyl ether/n-hexane to yield 8.10 g (71.3% of the theoretical yield) of acetohydroxamic acid in the form of colorless crystals melting at 141°-142° C.

$^1$H-NMR (DMSO-d$_6$):
2.05 (s, 3H, COCH$_3$);
2.10-2.16 (m, 2H, CH$_2$);
2.71-2.77 (m, 2H, CH$_2$);
3.73 (s, 3H, OCH$_3$);
4.22 (s, 2H, NCH$_2$);
6.28 (s, 1H, olefin.);
6.67-6.71 (m, 2H, aromat.);
6.95, 6.98 (d, 1H, aromat.)

EXAMPLE 2

N-[1-(6-methoxy-3,4-dihydronaphth-2-yl)ethyl-]acetohydroxamic acid a) 2-(1-hydroxyethyl)-6-methoxy-3,4-dihydronaphthalene A solution of 18.82 g of the aldehyde prepared according to Example 1b in 100 ml of absolute diethyl ether was added dropwise with stirring to a Grignard-solution of 2.93 g of magnesium chips and 7.5 ml of methyl iodide in 60 ml of absolute diethyl ether at a temperature between 0° and 5° C. The mixture was stirred at a temperature of 5° C. to complete the reaction (TLC: petroleum ether/diethyl ether—1:2). After hydrolysis by adding 100 ml of an aqueous saturated solution of ammonium chloride, the organic layer was separated and the aqueous layer extracted twice with 50 ml portions of diethyl ether. The combined organic extracts were washed with an aqueous saturated solution of sodium chloride and dried over sodium sulfate. After chromatography with petroleum ether/diethyl ether (1:1) 18.29 g (89.5% of the theoretical yield) of dihydronaphthalene were obtained in the form of yellow crystals melting at 32°–34° C.

$^1$H-NMR (CDCl$_3$):
1.34–1.36 (d, 3H, CH$_3$);
2.19–2.40 (m, 2H, CH$_2$);
2.78–2.83 (t, 2H, CH$_2$);
3.80 (s, 3H, OC$_3$);
4.40–4.46 (q, 1H, OCH);
6.39 (s, 1H, olefin.);
6.67–6.70 m, 2H, aromat.);
6.96–6.99 (m, 1H, aromat.).

b) 2-acetyl-6-methoxy-3,4-dihydronaphthalene

To a solution of 18.19 g of the dihydronaphthalene prepared according to Example 2a in 450 ml of absolute toluene were added in small portions at 20° C. while stirring under a dry nitrogen atmosphere 20.6 g of 2,3-dichloro-5,6-dicyano-p-benzoquinone (TLC: petroleum ether/diethyl ether—1:1). When the reaction was complete, the mixture was filtered and washed with toluene. After evaporation of the filtrate and chromatography with petroleum ether/diethyl ether (1:1) 15.36 g (85.3% of the theoretical yield) of 2-acetyl-6-methoxy-3,4-dihydronaphthalene were obtained in the form of pale yellow crystals melting at 70°–72° C.

$^1$H-NMR (CDCl$_3$):
2.42 (s, 3H, COCH$_3$);
2.54–2.57 (m, 2H, CH$_2$);
2.79–2.84 (m, 2H, C$_2$);
3.83 (s, 3H, OCH$_3$);
6.74–6.78 (m, 2H, aromat.);
7.17, 7.19 (d, 1H, aromat.);
7.38 (s, 1H, olefin.).

c) Oxime of 2-acetyl-6-methoxy-3,4-dihydronaphthalene

By using 15.27 g of the compound prepared according to Example 2b, 12 38 g of sodium acetate and 13.20 g of hydroxylamine hydrochloride and proceeding as described in Example 1c, 15.39 g 93.8% of the theoretical yield) of the oxime were obtained in the form of nearly colorless crystals melting at 160°–163° C.

$^1$H-NMR (CDCl$_3$):
2.17 (s 3H, NCCH$_3$);
2.60–2.65 (m, 2H, CH$_2$);
2.80–2.85 (m, 2H, CH$_2$);
3.81 (s, 3H, OCH$_3$);
6.71–6.73 (m, 2H, aromat.);
6.80 (s, 1H, olefin.);
7.05–7.09 (m, 1H, aromat.).

d) N-[1-(6-methoxy-3,4-dihydronaphth-2-yl)ethyl-]acetohydroxamic acid

In accordance with Example 1d, 15.21 g of the compound prepared according to Example 2c were reacted successively with 6.93 g of sodium cyanoborohydride, 16.8 ml of acetic anhydride and an aqueous solution containing 10% by weight sodium carbonate. After recrystallization from ethyl acetate/n-hexane 8.0 g (43.7% of the theoretical yield) of the acetohydroxamic acid were obtained in the form of colorless crystals melting at 164°–165° C.

$^1$H-NMR (DMSO-d$_6$):
1.29, 1.31 (d, 3H, CH$_3$);
2.03 (s, 3H, NCOCH$_3$);
2.01–2.24 (m, 2H, CH$_2$);
2.69–2.74 (m, 2H, CH$_2$);
3.73 (s, 3H, OCH$_3$);
5.06–5.17 (m, 1H, NCH);
6.29 (s, 1H, olefin.);
6.67–6.70 (m, 2H, aromat.);
6.97, 7.00 (d, 1H, aromat.).

EXAMPLE 3

N-hydroxy-N-[(6-methoxy-3,4-dihydronaphth-2-yl)methyl]urea

In accordance with Example 1d, 4.73 g of sodium cyanoborohydride were added to 10.16 g of the compound prepared according to Example 1c in 100 ml of acetic acid. When the reaction was complete, the mixture was evaporated, and the resulting residue was dissolved in 100 ml of ethyl acetate. The solution was washed with aqueous saturated solutions of sodium hydrogen carbonate and sodium chloride and then dried over sodium sulfate. After evaporation a viscous material was obtained which was diluted in 150 ml of absolute 1,4-dioxane. After adding 10.5 ml of trimethylsilyl isocyanate the mixture was heated under reflux for two hours. After cooling the mixture was washed with aqueous saturated solutions of ammonium chloride and sodium chloride and then dried over sodium sulfate. After evaporation and recrystallization from ethyl acetate, 6.79 g (54.7% of the theoretical yield) of the urea were obtained in the form of colorless crystals which decomposed at 139°–140° C.

$^1$H-NMR (DMSO-d$_6$):
2.14–2.19 (m, 2H, CH$_2$);
2.71–2.77 (m, 2H, CH$_2$);
3.73 s, 3H, OCH$_3$);
4.06 (s, 2H, NCH$_2$);
6.29 (s, 1H, olefin.);
6.33 (s, 2H, CONH$_2$);
6.66–6.70 (m, 2H, aromat.);
6 92, 6.95 (d, 1H, aromat.).

EXAMPLE 4

N-[(6-n-butoxy-3,4-dihydronaphth-2-yl)methyl-]acetohydroxamic acid a) 6-hydroxy-1-tetralone A mixture of 50 g of 6-methoxy-1-tetralone, 200 ml of acetic acid and 400 ml of hydrobromic acid (47% HBr) was heated under reflux for 24 hours. After cooling, the reaction mixture was poured into 3 liters of water, solid matter was filtered out, and the resulting filtrate was extracted three times with ethyl acetate. The extracts were washed with an aqueous solution of sodium carbonate, dried over sodium sulfate and evaporated. The resulting residue together with the filtered solid matter was recrystallized from ethyl acetate to yield 40.75 g (89.5% of the theoretical yield) of 6-hydroxy-1-tetralone in the form of reddish-brown crystals melting at 153°-155° C.

$^1$H-NMR (CDCl$_3$):
2.07-2.15 (m, 2H, CH$_2$);
2.62-2.66 (t, 2H, CH$_2$);
2.89-2.93 (t, 2H, CH$_2$);
6.72, 6.73 (d, 1H, aromat.);
6.80-6.83 (d,d, 1H, aromat.);
7.97, 8.00 (d, 1H, aromat.).

b) 6-n-butoxy-1-tetralone

A solution of 2.50 g of 6-hydroxy-1-tetralone in 20 ml of acetone, 2.54 g of potassium carbonate and 2 ml of 1-bromobutane were heated under reflux for four days. After evaporation the residue was diluted carefully in 20 ml of 1N hydrochloric acid and extracted three times with ethyl acetate. Then the extracts were washed with aqueous saturated solutions of sodium hydrogen carbonate and sodium chloride and dried over sodium sulfate. After evaporation the resulting residue was purified by chromatography with diethyl ether/petroleum ether (1:2) to yield 3.08 g (91.5% of the theoretical yield) of 6-n-butoxy-1-tetralone in the form of a nearly colorless oil.

$^1$H-NMR (CDCl$_3$):
0.96-1.01 (t, 3H, CH$_3$);
1.43-1.56 (m, 2H, CH$_2$);
1.73-1.83 (m, 2H, CH$_2$);
2.07-2.15 (m, 2H, CH$_2$);
2.58-2.63 (t, 2H, CH$_2$);
2.89-2.94 (t, 2H, CH$_2$);
3.99-4.03 (t, 2H, OCH$_2$);
6.69, 6.70 (d, 1H, aromat.);
6.79-6.83 (d,d, 1H, aromat.);
7.98, 8.01 (d, 1H, aromat.).

6-n-butoxy-1-tetralone was obtained in a yield of 88% by using 1-iodobutane instead of 1-bromobutane.

c) 6-n-butoxy-1-hydroxy-1,2,3,4-tetrahydronaphthalene

A solution of 21.9 g of the compound prepared according to Example 4b in 300 ml of ethanol was reacted as described in Example 1a with 7.65 g of sodium borohydride. After chromatography with petroleum ether/diethyl ether (1:1) 21.15 g (96.0% of the theoretical yield) of the desired compound were obtained, which solidified slowly and melted at 38°-40° C.

$^1$H-NMR (CDCl$_3$):
0.94-0.99 (t, 3H, CH$_3$);
1.44-1.54 (m, 2H, CH$_2$);
1.68-1.81 (m, 2H, CH$_2$);
1.85-2.02 (m, 2H, CH$_2$);
2.63, 2.82 (m, 2H, CH$_2$);
3.92-3.96 (t, 2H, OCH$_2$);
4.70-4.76 (m, 1H, OCH);
6.61, 6.62 (d, 1H; aromat.);
6.74-6.77 (d,d, 1H, aromat.);
7.30, 7.33 (d, 1H, aromat.).

d) 6-n-butoxy-3,4-dihydro-2-naphthaldehyde

As described in Example 1b, 21.15 g of the compound prepared according to Example 4c were reacted with 14.3 ml of phosphorus oxychloride and 20.9 ml of dimethylformamide. After chromatography with petroleum ether/diethyl ether (2:1), 19.35 g 87.5% of the theoretical yield) of the naphthaldehyde were obtained in the form of colorless crystals melting at 62°-64° C.

$^1$H-NMR (CDCl$_3$):
0.96-1.01 (t, 3H, CH$_3$);
1.44-1.56 (m, 2H, CH$_2$);
1.71-1.82 (s, 2H, CH$_2$);
2.52-2.57 (m, 2H, CH$_2$);
2.81-2.87 (m, 2H, CH$_2$);
3.97-4.01 (t, 2H, OCH$_2$);
6.75-6.78 (m, 2H, aromat.,olefin.);
7.20-7.23 (m, 2H, aromat.);
9.61 (s, 1H, CHO).

e) 6-n-butoxy-3,4-dihydro-2-naphthaldehyde-oxime

As described in Example 1c, 19.12 g of the compound prepared according to Example 4d were reacted with 8.7 g of hydroxylamine hydrochloride and 8.15 g of sodium acetate to yield 18.83 g (92.5% of the theoretical yield) of the oxime in the form of a white powder melting at 116°-118° C.

$^1$H-NMR (CDCl$_3$):
0.95-1.00 (t, 3H, CH$_3$);
1.43-1.55 (m, 2H, CH$_2$);
1.72-1.81 (m, 2H, CH$_2$);
2.55-2.60 (m, 2H, CH$_2$);
2.8-2.87 (m, 2H, CH$_2$);
3.94-3.99 (t, 2H, OCH$_2$);
6.61 (s, 1H, olefin.);
6.68-6.71 (m, 2H, aromat.);
7.02, 7.05 (d, 1H, aromat.);
7.89 (s, 1H, N=CH).

f) N-[(6-n-butoxy-3,4-dihydronaphth-2-yl)methyl]acetohydroxamic acid As described in Example 1d, 18.4 g of the compound prepared according to Example 4e were reacted with 7.16 g of sodium cyanoborohydride and 18 ml of acetic anhydride. The O-acetylated acetohydroxamic acid was isolated by chromatography (petroleum ether/diethyl ether—1:3) and selectively hydrolyzed with an aqueous solution of sodium carbonate. Recrystallization from ethyl acetate/n-hexane yielded 13.72 g (63.2% of the theoretical yield) of the hydroxamic acid in the form of colorless crystals melting at 97°-98° C.

$^1$H-NMR (DMSO-d$_6$):
0.91-0.96 (t, 3H, CH$_3$);
1.39-1.49 (m, 2H, CH$_2$);
1.63-1.70 (m, 2H, CH$_2$);
2.04 (s, 3H, COCH$_3$);
2.10-2.15 (m, 2H, CH$_2$);
2.70-2.76 (m, 2H, CH$_2$);
3.91-3.95 (t, 2H, OCH$_2$);
4.21 (s, 2H, NCH$_2$);
6.28 (s, 1H, olefin.);
6.65-6.70 (m, 2H, aromat.);
6.93, 6.95 (d, 1H, aromat.).

EXAMPLE 5

N-hydroxy-N-[(6-cyclopentyloxy-3,4-dihydronaphth-2-yl)methyl]urea a) 6-cyclopentyloxy-1-tetralone As described in Example 4b, 13.0 g of the compound prepared according to Example 4a and 10.5 ml of chlorocyclopentane were reacted in 65 ml of acetone in the presence of 13.8 g of potassium carbonate. After working up the reaction mixture and purifying the product, 14.65 g (79.5% of the theoretical yield) of the desired compound were obtained in the form of a yellow oil.

$^1$H-NMR (CDCl$_3$):

1.57–2.01 (m, 8H, CH$_2$);
2.06–2.15 (m, 2H, Cl$_2$);
2.57–2.62 (m, 2H, CH$_2$);
2.88–2.92 (m, 2H, CH$_2$);
4.70–4.84 (m, 1H, OCH);
6.66, 6.67 (d, 1H, aromat.);
6.76–6.80 (d,d, 1H, aromat.);
7.97, 8.00 (d, 1H, aromat.).

b) 6-cyclopentyloxy-1-hydroxy-1,2,3,4-tetrahydronaphthalene

To a solution of 1.52 g of lithium aluminium hydride in 75 ml of absolute diethyl ether was added while stirring a solution of 16.45 g of the compound prepared according to Example 5a in 30 ml of diethyl ether in such a manner that the reaction mixture simmered. After heating under reflux for 3 hours, excess hydride was decomposed by carefully adding water. The ether layer was separated, and the aqueous layer extracted three times with 20 ml portions of diethyl ether. The combined organic layers were washed with an aqueous saturated solution of sodium chloride and then dried over sodium sulfate. After evaporation and chromatographic purification with petroleum ether/diethyl ether (1:1), 12.32 g (74.2% of the theoretical yield) of the desired compound were obtained in the form of a reddish oil.

$^1$H-NMR (CDCl$_3$):
1.52–2.02 (m, 12H, CH$_2$);
2.61–2.86 (m, 2H, CH$_2$);
4.68–4.80 (m, 1H, OCH);
6.59, 6.60 (d, 1H, aromat.);
6.71–6.75 (d,d, 1H, aromat.);
7.29, 7.32 (d, 1H, aromat.).

c) 6-cyclopentyloxy-3,4-dihydronaphth-2-aldehyde

To 10.2 g of the compound prepared according to Example 5b in 15 ml 1,2-dichlorobenzene were added 6 ml of N-methyl formanilide and then dropwise 4.5 ml of phosphorus oxychloride. The mixture was stirred in a weak nitrogen flow at a bath temperature of 65° C. (TLC: petroleum ether/diethyl ether—2:1). When the reaction was complete, a solution of 28 g of sodium acetate in 65 ml of water was added dropwise at 20° C. Then the mixture was extracted three times with 30 ml portions of ethyl acetate. The extracts were washed with an aqueous saturated solution of sodium chloride, dried over sodium sulfate and evaporated. Chromatography of the resulting residue with petroleum ether/diethyl ether (1:1) yielded 7.37 g (69.3% of the theoretical yield) of the aldehyde in the form of a yellow viscous material.

$^1$H-NMR (CDCl$_3$):
1.55–2.00 (m, 8H, CH$_2$);
2.52–2.57 (m, 2H, CH$_2$);
2.81–2.86 (m, 2H, CH$_2$);
4.76–4.84 (m, 1H, OCH);
6.72–6.75 (m, 2H, aromat., olefin.);
7.19–7.23 (m, 2H, aromat.);
9.79 (s, 1H, CHO).

d) 6-cyclopentyloxy-3,4-dihydronaphth-2-aldehyde-oxime

A mixture of 5.2 g of hydroxylamine hydrochloride, 7.27 g of the compound prepared according to Example 5c, 6.38 g of sodium carbonate and 120 ml of ethanol/water (2:1) was stirred at 50° C. for 6 hours, then added to 250 ml of an aqueous saturated solution of sodium chloride and extracted three times with 100 ml portions of ethyl acetate. The extracts were washed with an aqueous saturated solution of sodium chloride, dried over magnesium sulfate and evaporated to yield 7.46 g (96.6% of the theoretical yield) of the oxime in the form of a pale yellow powder melting at 166°–168° C.

$^1$H-NMR (CDCl$_3$):
1.57–1.97 (m, 8H, CH$_2$);
2.54–2.60 (m, 2H, CH$_2$);
2.80–2.86 (m, 2H, CH$_2$);
4.71–4.80 (m, 1H, OCH);
6.60 (s, 1H, olefin.);
6.66–6.69 (m, 2H, aromat.);
7.01–7.04 (m, 1H, aromat.);
7.89 (s, 1H, N=CH).

e) N-hydroxy-N-[(6-cyclopentyloxy-3,4-dihydronaphth-2-yl)-methyl]urea

To a solution of 7.20 g of the compound prepared according to Example 5d in 140 ml of ethanol were added at 0° C. 5.26 g of borane-trimethylamine complex and stirred for one hour. Then 70 ml of 20% by weight hydrochloric acid were added dropwise, and while stirring the mixture was heated to 20° C. (TLC: ethyl acetate/methanol—30:1). After the reduction was complete, the mixture was evaporated under vacuum, the resulting residue was diluted with water, and after addition of potassium carbonate up to a pH-value of 9 the mixture was extracted three times with ethyl acetate. The extracts were washed with an aqueous saturated solution of sodium chloride and dried over sodium sulfate. The residue obtained after evaporation was diluted with 100 ml of absolute tetrahydrofuran, and after addition of 3.8 ml of trimethylsilylisocyanate stirred at 50° C. for three hours. Then the mixture was diluted with 50 ml of ethyl acetate, washed with aqueous saturated solutions of ammonium and sodium chloride and dried over sodium sulfate. The residue obtained after evaporation was suspended in diethyl ether, the solids were filtered out, washed with diethyl ether and recrystallized from ethyl acetate/n-hexane to yield 5.31 g (62.7% of the theoretical yield) of the urea in the form of colorless crystals melting at 145°–147° C.

$^1$H-NMR (DMSO-d$_6$):
1.50–1.77 (m, 6H, CH$_2$);
1.81–1.96 (m, 2H, CH$_2$);
2.13–2.18 (m, 2H, CH$_2$);
2.69–2.75 (m, 2H, CH$_2$);
4.05 (s, 2H, NCH$_2$);
4.73–4.80 (m, 1H, OCH);
6.27 (s, 1H, olefin.);
6.34 (s, 2H, CONH$_2$);
6.61–6.65 (m, 2H, aromat.);
6.89, 6.92 (d, 1H, aromat.).

EXAMPLE 6

Proceeding as described in Examples 1 through 5 but using the appropriate reactants there were obtained:

a) N-[(6-cyclopentyloxy 3,4-dihydronaphth 2 yl)methyl]acetohydroxamic acid

Melting point: 110°–111° C.

$^1$H-NMR (DMSO-d$_6$):
1.31–1.95 (m, 8H, CH$_2$);
2.04 (s, 3H, COCH$_3$);
2.10–2.15 (t, 2H, CH$_2$);
2.70–2.75 (t, 2H, CH$_2$);
4.21 (s, 2H, NCH$_2$);
4.74–4.80 (m, 1H, OCH);
6.27 (s, 1H, olefin.);
6.62–6.66 (m, 2H, aromat.);
6.92, 6.94 (d, 1H, aromat.).

b) N hydroxy N [1 (6 methoxy 3,4-dihydronaphth 2 yl)ethyl]urea

Melting point: 146 148° C. (decomposition)
$^1$H-NMR (DMSO-d$_6$):
1.23, 1.25 (d, 3H, NCCH$_3$);
2.06–2.32 (m, 2H, CH$_2$);
2.62–2.77 (m, 2H, CH$_2$);
3.72 (s, 3H, OCH$_3$);
4.74–4.80 (m, 1H, NCH);
6.27 (s, 1H, olefin.);
6.31 (s, 2H, CONH$_2$);
6.66–6.70 (m, 2H, aromat.);
6.95, 6.98 d, 1H, aromat.).

c) N-hydroxy-N-[(6-n-butoxy-3,4-dihydronaphth-2-yl)methyl]urea

Melting point: 150°–152° C. (decomposition)
$^1$H-NMR (DMSO-d$_6$):
0.91–0.95 (t, 3H, CH$_3$);
1.37–1.49 (m, 2H, CH$_2$);
1.63–1.72 (m, 2H, CH$_2$);
2.13–2.19 (t, 2H, CH$_2$);
2.70–2.76 (t, 2H, CH$_2$);
3.90–3.94 (t, 2H, OCH$_2$);
4.06 (s, 2H, NCH$_2$);
6.28 (s, 1H, olefin.);
6.34 (s, 2H, CONH$_2$);
6.64–6.69 (m, 2H, aromat.);
6.90, 6.93 (d, 1H, aromat.).

d) N-hydroxy-N-[(6-allyloxy-3,4-dihydronaphth-2-yl)methyl]urea

Melting point: 148°–149° C. (decomposition)
$^1$H-NMR (DMSO-d$_6$):
2.15–2.20 (t, 2H, CH$_2$);
2.71–2.77 (t, 2H, CH$_2$);
4.07 (s, 2H, NCH$_2$);
4.51, 4.53 (d, 2H, OCH$_2$);
5.22–5.41 (m, 2H, olefin.);
5.96–6.09 (m, 1H, olefin.);
6.29 (s, 1H, olefin.);
6.32 (s, 2H, CONH$_2$);
6.67–6.71 (m, 2H, aromat.);
6.91, 6.93 (d, 1H, aromat.).

e) N-hydroxy-N-[(6-isopropoxy-3,4-dihydronaphth-2-yl)methyl]urea

Melting point: 136° C. (decomposition)
$^1$H-NMR (DMSO-d$_6$):
1.23, 1.25 (d, 6H, CH$_3$);
2.12–2.18 (t, 2H, CH$_2$);
2.69–2.75 (t, 2H, CH$_2$);
4.05 (s, 2H, NCH$_2$);
4.50–4.62 (m, 1H, OCH);
6.28 (s, 1H, olefin.);
6.34 (s, 2H, CONH$_2$);
6.64–6.68 (m, 2H, aromat.);
6.90, 6.93 (d, 1H, aromat.)

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A substituted 3,4-dihydronaphthalene corresponding to the formula I

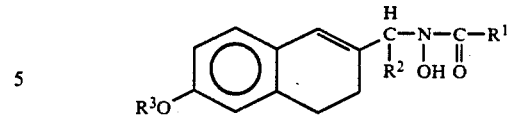

wherein
$R^1$ is a methyl group or an amino group;
$R^2$ represents a hydrogen atom or a methyl group, and
$R^3$ is a linear or branched chain alkyl group having 1 to 4 carbon atoms, an allyl or crotyl group, or a cyclopentyl group.

2. A substituted 3,4-dihydronaphthalene according to claim 1, wherein $R^3$ represents a methyl group.

3. A substituted 3,4-dihydronaphthalene according to claim 1, wherein $R^1$ represents an amino group.

4. A substituted 3,4-dihydronaphthalene according to claim 1, wherein $R^1$ represents an amino group, $R^2$ represents a hydrogen atom, and $R^3$ represents a methyl group.

5. A pharmaceutical composition for parenteral, oral, rectal, topical or intranasal administration comprising an effective 5-lipoxygenase inhibiting amount of at least one substituted 3,4-dihydronaphthalene according to claim 1, and at least one pharmaceutical carrier or excipient.

6. A pharmaceutical composition according to claim 5, containing from 0.01 to 1000 mg of said at least one substituted 3,4-dihydronaphthalene per unit dose.

7. A parenteral pharmaceutical composition according to claim 5, comprising a sterile, pharmaceutically acceptable isotonic liquid vehicle suitable for parenteral administration containing from 0.1 to 1000 mg of said at least one substituted 3,4-dihydronaphthalene per unit dose.

8. An orally administrable pharmaceutical composition according to claim 5, comprising a tablet, dragee or capsule containing from 0.1 to 1000 mg of said at least one substituted 3,4-dihydronaphthalene.

9. A pharmaceutical composition according to claim 8, wherein at least a portion of said substituted 3,4-dihydronaphthalene is in delayed release form.

10. A pharmaceutical composition according to claim 5, containing said at least one substituted 3,4-dihydronaphthalene in spray-form suitable for intranasal or oral administration.

11. A process for preparing a pharmaceutical composition according to claim 5, comprising admixing an effective 5-lipoxygenase inhibiting amount of said at least one substituted 3,4-dihydronaphthalene with a pharmaceutically acceptable carrier, diluent or solvent, and preparing a desired dosage form from the resulting admixture.

12. A process according to claim 11, wherein said admixture further comprises at least one pharmacologically acceptable adjuvant selected from the group consisting of binders, lubricants, and tablet disintegrating agents.

13. A method for treating a patient suffering from a disorder attributable to the action of a leucotriene comprising administering to said patient an effective 5-lipoxygenase inhibiting amount of at least one substituted 3,4-dihydronaphthalene corresponding to the formula I

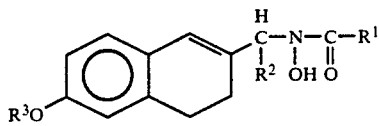

wherein
R[1] is a methyl group or an amino group;
R[2] represents a hydrogen atom or a methyl group, and
R[3] is a linear or branched chain alkyl group having 1 to 4 carbon atoms, an allyl or crotyl group, or a cyclopentyl group.

14. A method of treating a patient suffering from asthma comprising administering to said patient an effective anti-asthma amount of at least one substituted 3,4-dihydronaphthalene corresponding to the formula I

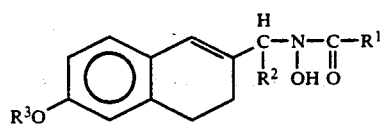

wherein
R[1] is a methyl group or an amino group;
R[2] represents a hydrogen atom or a methyl group, and
R[3] is a linear or branched chain alkyl group having 1 to 4 carbon atoms, an allyl or crotyl group, or a cyclopentyl group.

* * * * *